United States Patent
Orten

(10) Patent No.: US 6,619,126 B2
(45) Date of Patent: Sep. 16, 2003

(54) MECHANO-ELECTRICAL SENSOR

(75) Inventor: Birger Orten, Ålesund (NO)

(73) Assignee: Meditron AS, Vettre (NO)

( * ) Notice: Subject to any disclaimer, the term of this patent is extended or adjusted under 35 U.S.C. 154(b) by 0 days.

(21) Appl. No.: 09/886,376

(22) Filed: Jun. 22, 2001

(65) Prior Publication Data

US 2002/0043110 A1 Apr. 18, 2002

Related U.S. Application Data

(60) Provisional application No. 60/213,477, filed on Jun. 23, 2000.

(51) Int. Cl.$^7$ ................................................ G01N 29/00
(52) U.S. Cl. ............................ 73/649; 73/1.48; 73/584; 73/662
(58) Field of Search .................... 73/647, 662, 584, 73/573, 862.043, 1.48, 11.03, 11.01

(56) References Cited

U.S. PATENT DOCUMENTS

| | | | | |
|---|---|---|---|---|
| 2,880,333 A | | 3/1959 | Dranetz ...................... 310/326 |
| 4,051,395 A | | 9/1977 | Taylor ........................ 310/329 |
| 4,727,279 A | | 2/1988 | Peng .......................... 310/329 |
| 4,839,872 A | | 6/1989 | Gragnolati et al. ......... 367/180 |
| 5,531,115 A | * | 7/1996 | Erdley ....................... 73/504.2 |
| 5,571,972 A | * | 11/1996 | Okada ................... 73/862.043 |
| 5,581,013 A | * | 12/1996 | Frederick ................... 73/11.03 |
| 5,668,318 A | * | 9/1997 | Okada ...................... 73/504.11 |
| 5,682,000 A | * | 10/1997 | Okada ................... 73/862.043 |
| 5,780,749 A | * | 7/1998 | Okada ................... 73/862.043 |
| 5,996,412 A | * | 12/1999 | Hansen ..................... 73/514.34 |
| 6,038,924 A | * | 3/2000 | Lee et al. ................ 73/514.34 |
| 6,209,395 B1 | * | 4/2001 | Kristensen ............... 73/514.34 |
| 6,227,050 B1 | * | 5/2001 | Fujii et al. ................. 73/514.2 |
| 6,279,395 B1 | * | 8/2001 | Insalaco et al. .......... 73/514.34 |
| 6,386,035 B2 | * | 5/2002 | Janiaud et al. ........... 73/514.29 |
| 6,397,677 B1 | * | 6/2002 | Kinsley et al. .......... 73/514.34 |

FOREIGN PATENT DOCUMENTS

| | | |
|---|---|---|
| EP | 0 118 329 | 9/1984 |
| GB | 2 055 018 | 2/1981 |
| GB | 2 180 346 | 3/1987 |

* cited by examiner

Primary Examiner—Hezron Williams
Assistant Examiner—Jacques Saint-Surin
(74) Attorney, Agent, or Firm—Wenderoth, Lind & Ponack, L.L.P.

(57) ABSTRACT

A mechano/electrical sensor senses force or vibration and delivers at least one electrical signal that is a function of the sensed force or vibration. The sensor has at least one inner body supported by at least one piece of electric support structure that, in turn, is suspended in a surrounding framework. Signal leads are provided from opposite lead polarizable sides of the at least one support structure.

20 Claims, 4 Drawing Sheets

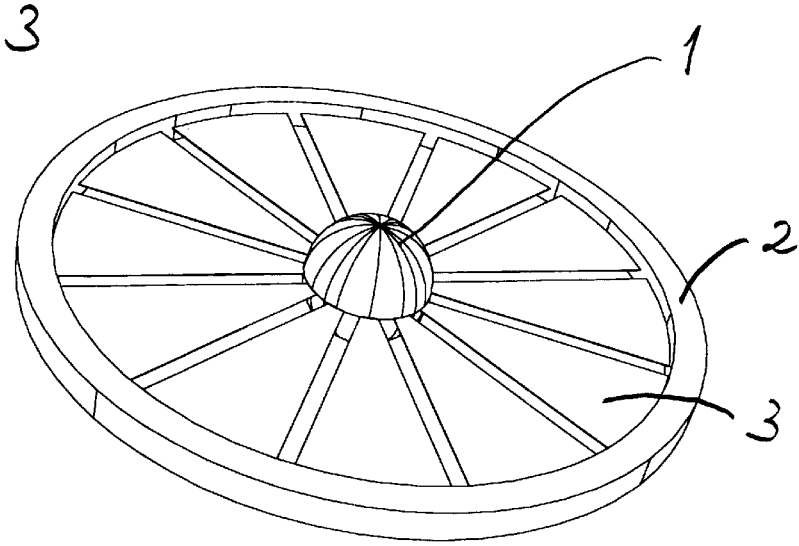
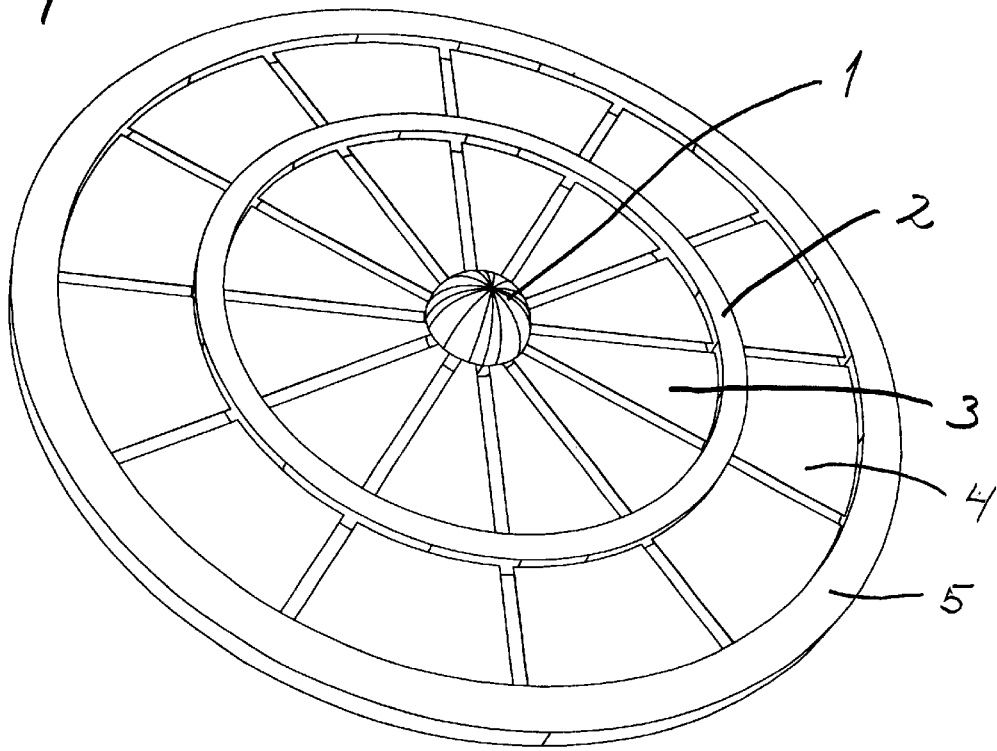

MECHANO-ELECTRICAL SENSOR

This application claims benefit of prior provisional application Ser. No. 60/213,477, filed Jun. 23, 2000.

BACKGROUND OF THE INVENTION

The present invention relates to sensing force or vibration, and delivering electrical signals representative of the sensed force or a parameter of a vibration state. More particularly, the invention relates to a mechano-electrical sensor for sensing force or vibration and delivering at least one electrical signal that is a function of the sensed force or vibration.

Force sensors, acceleration sensors and vibration sensors have many uses, and exist in many embodiments. Usually, two or three separate sensors are utilized (e.g., to sense acceleration in three orthogonal directions) by allowing massive bodies, suspended in spring systems, to move relative to respective reference frames. Rotation is usually sensed with a gyroscope device.

SUMMARY OF THE INVENTION

The present invention provides a sensor that, better than previously known solutions, is able to operate with a directional effect and provide good measurements regarding translation as well as rotation, by means of one movable body only. Therefore, in accordance with the invention, there is provided a mechano-electrical sensor such as described below.

BRIEF DESCRIPTION OF THE DRAWINGS

In the following, the invention will be illuminated further by describing exemplary embodiments of the invention with reference to the appended drawings, wherein

FIG. 3 shows another two-dimensional embodiment of the sensor in accordance with the invention;

FIG. 4 shows the same embodiment as FIG. 3, but suspended in an outer frame;

DETAILED DESCRIPTION OF THE INVENTION

Figure 1:
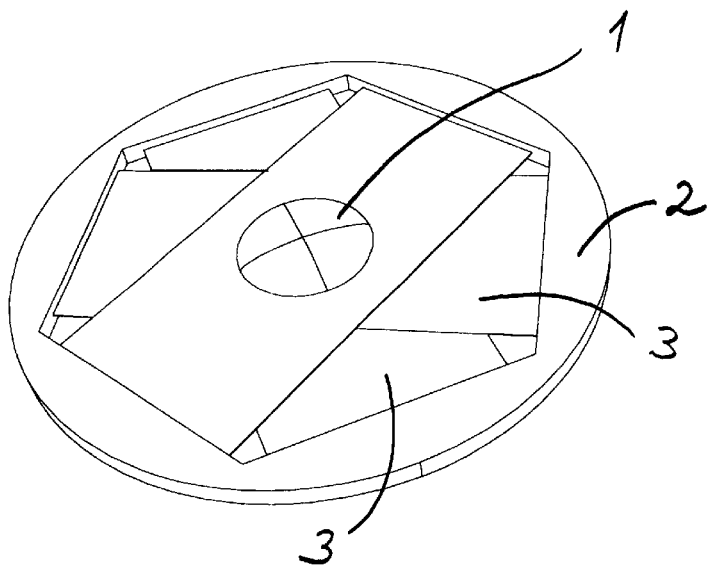
FIG. 1 shows a two-dimensional embodiment of the sensor in accordance with the invention.

In FIG. 1 appears a relatively simple, two-dimensional embodiment of the sensor of the present invention. An inner body 1 is supported by means of piezoelectric foils (i.e., a support structure) 3 in a frame 2, and non-appearing signal wires connected to respective sides of a foil 3 (which are oppositely polarizable) are able to deliver electrical signals generated when the foils are subject to deformation due to a shift of the inner body 1 relative to a relaxed center position. The figure shows three foils tautened in a hexagonal opening, but one single foil may be used, or a larger number of foils may be used. The choice of inner body will depend on the use field of the sensor. The inner body may, in uses including recording from soft surfaces, consist of plastic or silicone rubber with various shore values. In other applications, industrial diamond material may be used. Combinations of material and geometrical shapes of the inner body are important. The inner body may also include openings to provide a possibility for air passage therethrough, for example in microphone applications. The foils may be attached between two metallic frame parts that are insulated from each other and possibly from other frame parts along the periphery, so that signals can be collected from the metallic frame parts. When foils 3 are used as indicated in FIG. 1, the stretch directions of the foils may be along the longitudinal direction for each foil strip. This provides an opportunity to collect a higher, summed total signal compared to the case of only one single foil, either as a strip across the opening, or as a complete "diaphragm" covering the whole opening.

Figure 7:
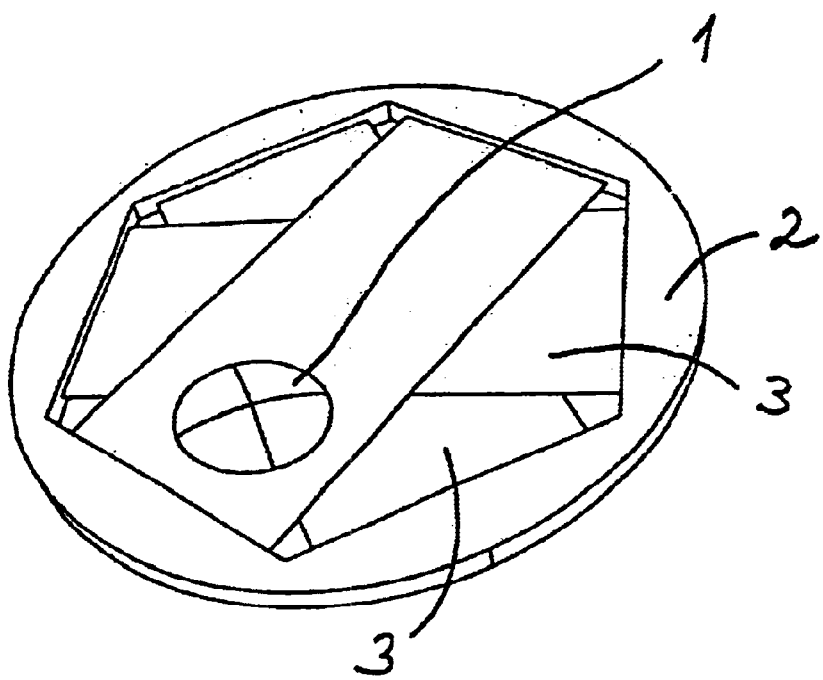
FIG. 7 shows another two-dimensional embodiment of the sensor in accordance with the invention, including a non-centered inner body.

Centering of the inner body 1 is not necessary, and one may visualize embodiments with an inner body arranged in an eccentric (non-centered) position as shown in FIG. 7. In addition, the shape of frame 2 is not crucial, as long as the frame is rigid and suitable for attaching the piezoelectric foils.

Such a two-dimensional sensor will clearly be most sensitive with regard to force or vibratory influence in a direction perpendicular to the plane spanned by the sensor. However, it will also be possible (when using several foils with separate signal wires) to sense a force in the support plane, i.e., lateral movement of the inner body. Thus, "two-dimensional" as used herein means that the sensor extends in a two-dimensional geometric plane, as shown in FIGS. 1–4. In contrast, the term "three-dimensional" as used herein refers to a sensor that extends in three dimensions, such as those shown in FIGS. 5 and 6.

Figure 2:
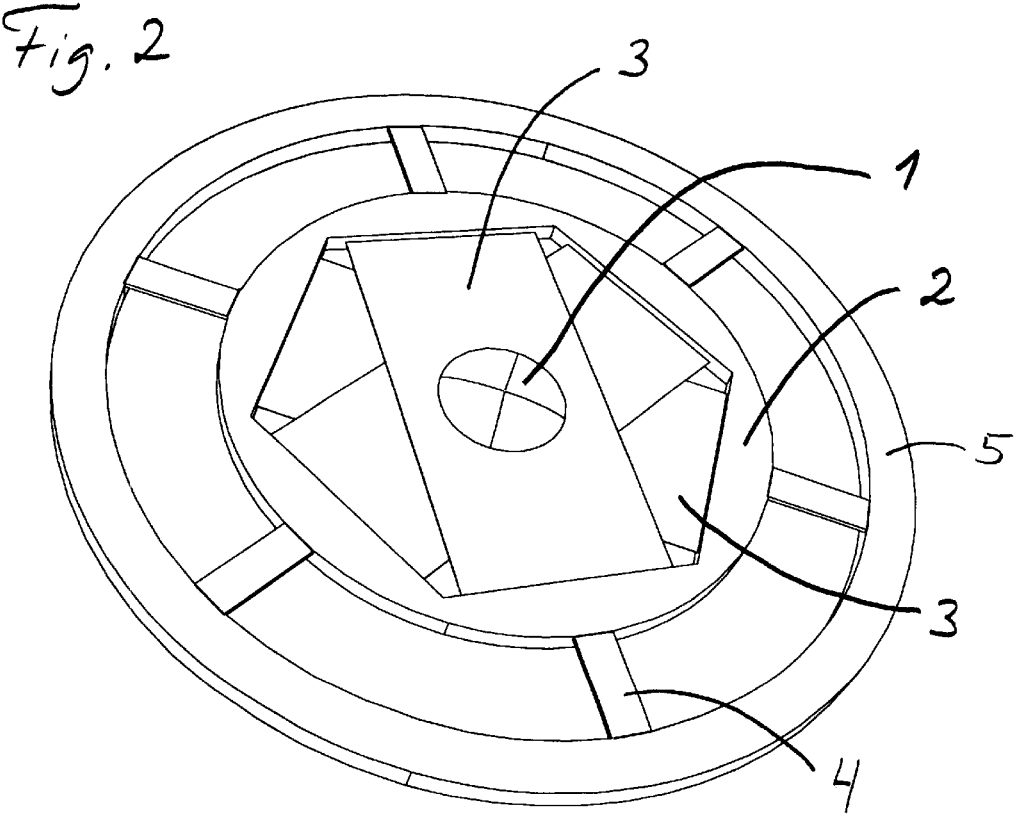
FIG. 2 shows the same embodiment as FIG. 1, but suspended in an outer frame.

FIG. 2 shows the same embodiment as in FIG. 1, but the whole basic sensor is suspended in an (second) outer frame 5. The suspension is by means of elastic elements 4, such as rubber elements, and such an embodiment of the invention will be particularly favorable when using the sensor as a sensor element in a microphone. The main purpose of the outer frame 5 is noise attenuation, i.e., attenuation of noise in the form of vibrations that may bring the piezo elements of the sensor into oscillation. When the sensor is attached to an outer frame 5, there will be two oscillatory systems, of which the inner system is the sensor itself. The design must then give the outer system a resonant frequency that is low relative to the resonant frequency of the inner system comprising inner (first) frame/piezoelectric suspension structure/inner body. The frame will then work as a low pass filter. This relates primarily to the two-dimensional solution.

Further, it will be of great importance whether it is the first frame 2 or the inner body 1 that is supposed to oscillate in relation to the surroundings. Ideally, it is desirable to maintain the first frame 2 at rest in relation to the surroundings, while the inner body oscillates relative to the frame. In practice, the suspension of the sensor frame will normally provide "good" acoustic coupling between the surroundings and the sensor elements, and normally this is not desirable. Generally, the mass of the inner body will influence the characteristic (the frequency response) most strongly, but design and material choice will also be of importance regarding the coupling between the "sensed medium" and the sensor. Due to the coupled oscillatory systems, the characteristic must be optimized as a function of mass ratios, stiffnesses etc.

In an application in a microphone that is supposed to be good at high frequencies, the oscillations in the air will bring the suspension diaphragms (see FIG. 4) into oscillation, and the frame 2 will then oscillate around the inner body 1. In such a case, the vibrating part of the sensor must be as light as possible.

FIG. 3 shows an alternative embodiment of the sensor in accordance with the invention, still in a two-dimensional version. An inner body 1 is suspended in a number of sector-shaped (wedge-shaped) piezoelectric foils 3 constituting a support structure. Preferably, the stretch direction for every foil sector is arranged in the same manner in relation to the radius in the respective position (for example, pointing substantially in a radial direction). There are small openings (i.e., gaps) between foils in this case, which in connection with use in a microphone, for example, may be favorable regarding air passage through the openings. Moreover, connection of signal leads is made in a similar manner as mentioned regarding FIG. 1, and it appears that it may be possible to achieve high sum voltages with appropriate coupling of signal leads from each respective foil sector, if this is desirable. Alternatively, separate signals can be collected from each respective sector.

FIG. 4 shows suspension in an outer (second) frame 5 in the same manner as in FIG. 2. However, in this case the suspension structures are elastic, sector-shaped diaphragms made of, for example, rubber.

Figure 5:
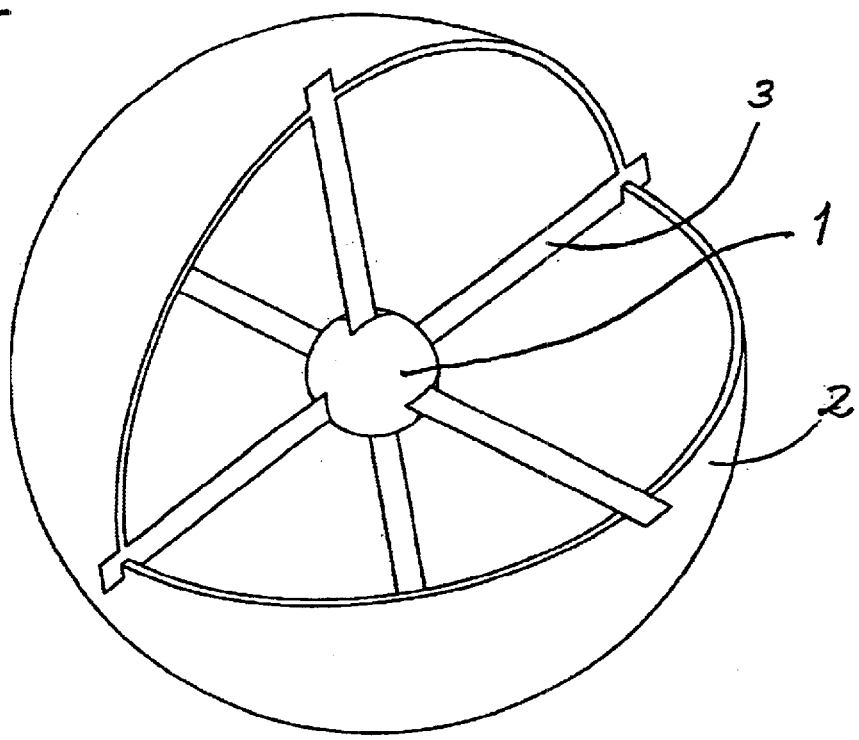
FIG. 5 shows a three-dimensional embodiment of the sensor in accordance with the invention, with foil-shaped support structures, in a partially cut-away view.

FIG. 5 shows an embodiment of a three-dimensional type. The inner body 1 is held suspended at the center of a spherical frame 2 by means of piezoelectric foil pieces (i.e., a support structure) 3 arranged in such a manner that a relative shifting of the inner body 1, or a rotation for that matter, will be detectable by means of voltages created in the foils 3. The voltages can be collected by means of (not shown) signal wires connected to the two sides of the foil pieces projecting out through the frame. Of course, frame 2 does not have to be spherical, nor does it need to be closed, but it is important that it is rigid, in order to constitute a reference for the position of the inner body.

Figure 6:
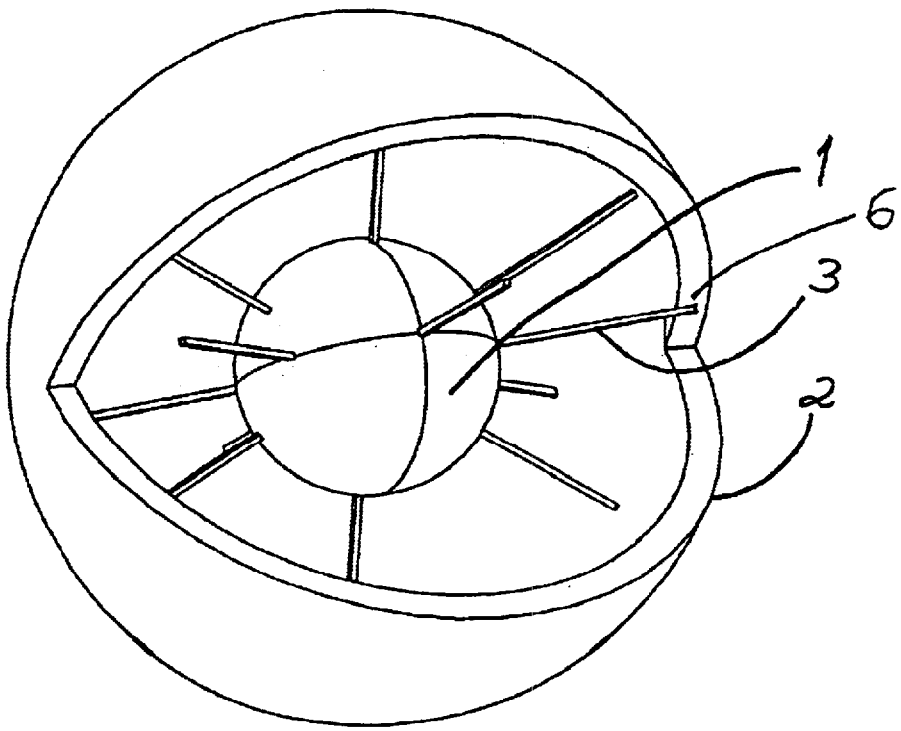
FIG. 6 shows another three-dimensional embodiment with filament-shaped support structures, this drawing also in a partially cut-away view.

FIG. 6 shows a similar design, but the piezoelectric foils have been replaced by filaments. The filaments are either a piezoelectric type with a function corresponding to the foil pieces in FIG. 5, or the filaments are taut and substantially inelastic, but attached to piezoelectric areas 6 of the frame 2. In other words, the frame itself has respective piezoelectric areas at suspension positions on the frame for the taut filaments (which constitute the support structure). These piezoelectric areas generate voltages depending on the translation or rotation of the inner body relative to frame 2.

Such a three-dimensional force/vibration sensor as shown in FIG. 5 and FIG. 6 is based upon a rigid coupling between the frame and the body for which force or possibly acceleration shall be measured. Thus, the inertia of the inner body will create the measurable voltages in the suspension structures 3 (foil or filaments) or in their piezoelectric attachment areas. Hence, with signal leads coupled to suitable processing equipment, such an acceleration/vibration sensor may constitute a main element in, for example, an inertia navigation system.

Also the three-dimensional embodiments shown in FIGS. 5 and 6 can be suspended in an outer framework via an elastic material (such as rubber) in two or three dimensions.

The foil pieces shown in the embodiment of FIG. 5 may come in other shapes, such as sector-like or possibly as approximations to full circle areas, and the planes to be spanned do not necessarily have to be orthogonal like in the figure.

In addition, foil materials or filament materials are not the only possible materials in this application, and the suspension structures between the inner body and fumes may possibly be piezoelectric bimorph elements or similar elements.

The invention is also intended to accommodate the variant that has already been mentioned, namely the variant with suspension structures that are not piezoelectric, but attached to piezoelectric areas of the framework.

What is claimed is:

1. A mechano-electrical sensor for sensing force or vibration, and for generating at least one electrical signal that is a function of the sensed force or vibration, comprising:
   a single inner body;
   a plurality of separate piezoelectric support foils supporting said inner body, each of said support foils having oppositely polarizable sides, having a sector shape, and having signal lead wires connected to said sides; and
   a frame surrounding and supporting said support foils, each of said support foils being connected to said frame and being connected to said inner body.

2. The sensor of claim 1, further comprising a central foil support piece connecting said inner body to each of said support foils.

3. The sensor of claim 1, wherein said frame extends in a two-dimensional plane.

4. The sensor of claim 3, wherein said support foils are arranged so as to extend in a radial direction from said inner body, said signal lead wires being arranged so as to add respective output signals from said support foils.

5. The sensor of claim 1, wherein said frame surrounds said inner body and said support foils support said inner body such that said inner body is non-centered within said frame.

6. The sensor of claim 1, wherein said frame extends in three dimensions.

7. The sensor of claim 6, wherein each of said support foils comprises a planar support foil, and said planar support foils are arranged so as to extend outward from said inner body in three dimensions.

8. The sensor of claim 7, wherein said planar support foils are arranged in three planes, said planes being orthogonal.

9. The sensor of claim 7, wherein said planar support foils are arranged in planes, said planar support foils in each plane being arranged such that a gap is formed between adjacent planar support foils.

10. The sensor of claim 1, wherein said frame comprises a first frame, further comprising a second outer frame, and comprising elastic material suspending said first frame within said second outer frame.

11. The sensor of claim 10, wherein said elastic material comprises an elastic membrane.

12. The sensor of claim 10, wherein said elastic material comprises a rubber material extending in three dimensions.

13. A mechano-electrical sensor for sensing force or vibration, and for generating at least one electrical signal that is a function of the sensed force or vibration, comprising:
   an inner body;
   a support structure supporting said inner body;
   a frame surrounding and supporting said support structure, said frame having piezoelectric areas at each of respective suspension locations on said frame whereat said support structure is supported by said frame; each of said piezoelectric areas having oppositely polarizable sides; and signal lead wires connected to said piezoelectric areas of said frame.

14. The sensor of claim 13, wherein said support structure comprises a plurality of taut and substantially inelastic filaments, each of said filaments being connected to said inner body and to a respective one of said suspension locations on said frame, each of said piezoelectric areas comprising a separate area surrounding a respective one of said suspension locations.

15. The sensor of claim 14, wherein said frame extends in a two-dimensional plane, each of said filaments extends in a radial direction from said inner body to said frame.

16. The sensor of claim 15, wherein said plurality of filaments comprise filaments having different lengths, said frame surrounding said inner body and said filaments supporting said inner body such that said inner body is non-centered within said frame.

17. The sensor of claim 14, wherein said frame extends in three dimensions.

18. The sensor of claim 13, wherein said frame comprises a first frame, further comprising a second outer frame, and comprising elastic material suspending said first frame within said second outer frame.

19. The sensor of claim 18, wherein said elastic material comprises an elastic membrane.

20. The sensor of claim 18, wherein said elastic material comprises a rubber material extending in three dimensions.

* * * * *